(12) United States Patent
Lauria

(10) Patent No.: US 8,303,881 B2
(45) Date of Patent: Nov. 6, 2012

(54) SUTURE CONTAINING BARBS

(75) Inventor: Paul Lauria, Clinton, CT (US)

(73) Assignee: Covidien LP, Mansfield, MA (US)

( * ) Notice: Subject to any disclaimer, the term of this patent is extended or adjusted under 35 U.S.C. 154(b) by 51 days.

(21) Appl. No.: 12/914,302

(22) Filed: Oct. 28, 2010

(65) Prior Publication Data

US 2012/0104644 A1    May 3, 2012

(51) Int. Cl.
B29C 53/14 (2006.01)
D01D 5/42 (2006.01)
(52) U.S. Cl. .................. 264/281; 264/145; 264/210.8
(58) Field of Classification Search .................... 264/281
See application file for complete search history.

(56) References Cited

U.S. PATENT DOCUMENTS

| | | | | |
|---|---|---|---|---|
| 2,456,344 | A * | 12/1948 | Vaala | 524/317 |
| 3,833,972 | A * | 9/1974 | Brumlik | 24/449 |
| 4,129,632 | A * | 12/1978 | Olson et al. | 264/40.1 |
| 5,342,376 | A | 8/1994 | Ruff | |
| 5,931,855 | A | 8/1999 | Buncke | |
| 6,165,202 | A | 12/2000 | Kokish et al. | |
| 6,203,564 | B1 | 3/2001 | Hutton et al. | |
| 6,241,747 | B1 | 6/2001 | Ruff | |
| 6,270,517 | B1 | 8/2001 | Brotz | |
| 6,599,310 | B2 | 7/2003 | Leung et al. | |
| 6,692,499 | B2 | 2/2004 | Törmälä et al. | |
| 6,773,450 | B2 | 8/2004 | Leung et al. | |
| 2002/0177876 | A1 | 11/2002 | Roby et al. | |
| 2003/0074023 | A1 | 4/2003 | Kaplan et al. | |
| 2003/0149447 | A1 | 8/2003 | Morency et al. | |
| 2004/0010275 | A1 | 1/2004 | Jacobs et al. | |
| 2004/0030354 | A1 | 2/2004 | Leung et al. | |
| 2004/0060409 | A1 | 4/2004 | Leung et al. | |
| 2004/0060410 | A1 | 4/2004 | Leung et al. | |
| 2004/0088003 | A1 | 5/2004 | Leung et al. | |
| 2004/0162580 | A1 | 8/2004 | Hain | |
| 2005/0033367 | A1 | 2/2005 | Leung et al. | |
| 2005/0267531 | A1 | 12/2005 | Ruff et al. | |
| 2006/0111734 | A1 | 5/2006 | Kaplan et al. | |
| 2006/0116718 | A1 | 6/2006 | Leiboff | |
| 2007/0005110 | A1 | 1/2007 | Collier et al. | |
| 2007/0187861 | A1 | 8/2007 | Genova et al. | |
| 2007/0224237 | A1 | 9/2007 | Hwang et al. | |
| 2008/0058869 | A1 | 3/2008 | Stopek et al. | |

(Continued)

FOREIGN PATENT DOCUMENTS

EP    0 499 048 A1    8/1992

(Continued)

OTHER PUBLICATIONS

"Suture", http://www.thefreedictionary.com/suture.*

Primary Examiner — Yogendra Gupta
Assistant Examiner — Alison Hindenlang

(57) ABSTRACT

Methods and systems of forming barbed sutures from blown films are provided. A method for forming a barbed suture includes providing a blown film, cutting slits into an outer edge of the blown film, and twisting the blown film such that the slits protrude from the twisted blown film to form a barbed suture. A system for forming a barbed suture includes a set of heating rollers configured for stiffening an outer edge of a blown film, a set of cutting rollers configured for forming slits in the outer edge, a set of twisting rollers configured for twisting the blown film into a suture, and a heat source to set the suture.

13 Claims, 4 Drawing Sheets

U.S. PATENT DOCUMENTS

| | | |
|---|---|---|
| 2009/0076543 A1 | 3/2009 | Maiorino et al. |
| 2009/0210003 A1 | 8/2009 | Sulamanidze et al. |

FOREIGN PATENT DOCUMENTS

| | | |
|---|---|---|
| EP | 1 656 890 A3 | 5/2006 |
| WO | WO 98/52473 | 11/1998 |
| WO | WO 03/001979 A2 | 1/2003 |
| WO | WO 2004/014236 A1 | 2/2004 |
| WO | WO 2004/030520 A2 | 4/2004 |
| WO | WO 2004/030704 A2 | 4/2004 |
| WO | WO 2004/030705 A2 | 4/2004 |
| WO | WO 2006/079469 A1 | 8/2006 |
| WO | WO 2008/117328 A2 | 10/2008 |
| WO | WO 2008/141034 A1 | 11/2008 |

* cited by examiner

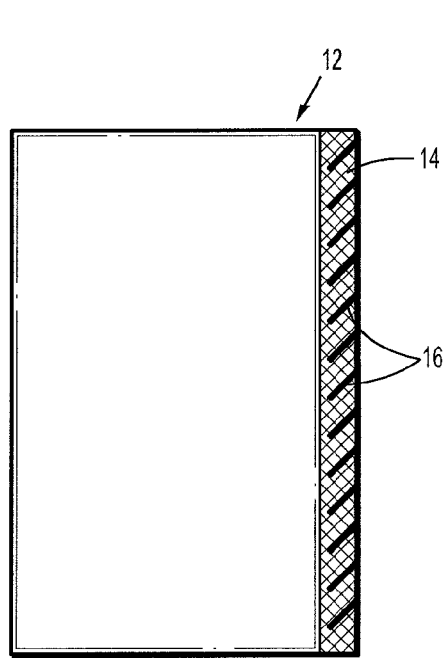
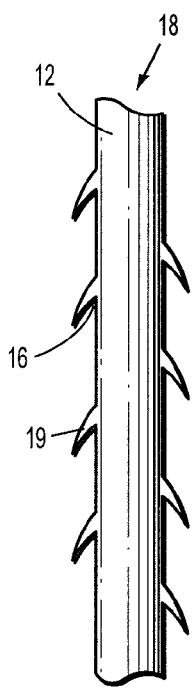
FIG. 3A  FIG. 3B
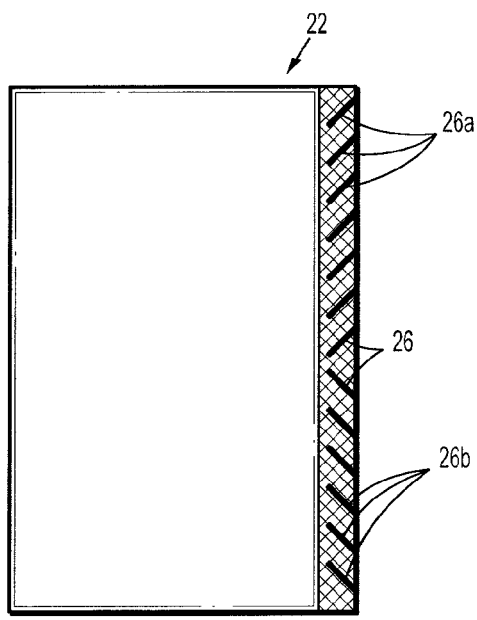
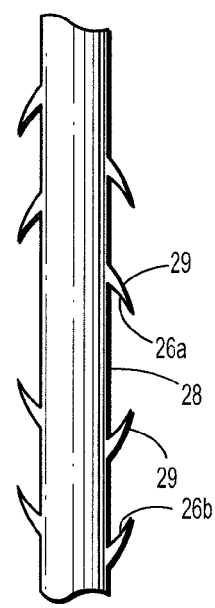
FIG. 4A  FIG. 4B

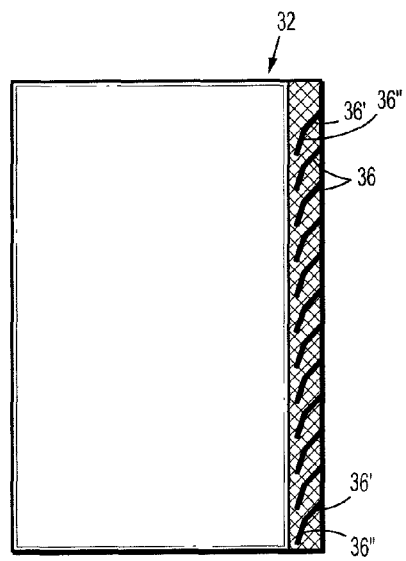
FIG. 5
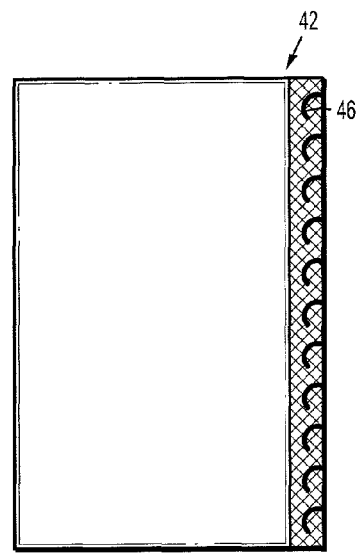
FIG. 6
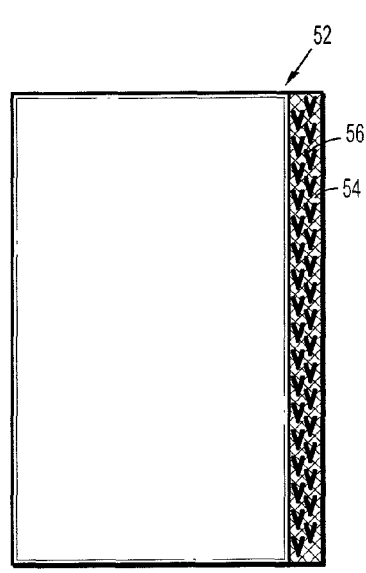
FIG. 7A
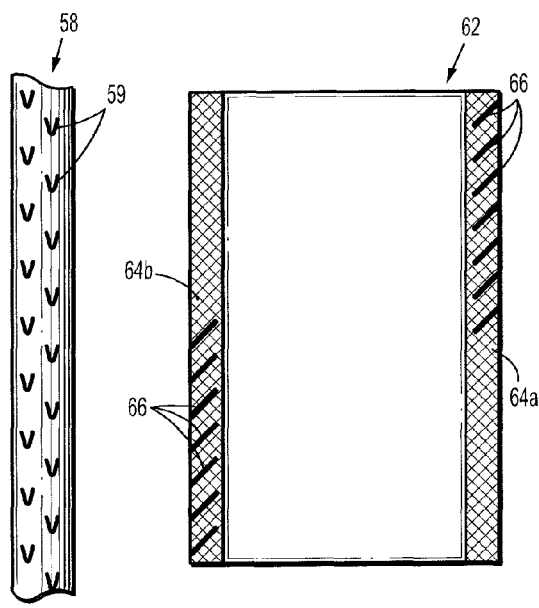
FIG. 7B   FIG. 8

SUTURE CONTAINING BARBS

BACKGROUND

1. Technical Field

The present disclosure relates to barbed sutures. More particularly, the present disclosure relates to systems and methods of forming barbed sutures from blown films.

2. Background of Related Art

Methods of forming barbed sutures are known. Typically, sutures are made from filaments, and methods for making such sutures generally include the steps of extruding at least one bioabsorbable or nonbioabsorbable polymer to provide filaments, drawing or stretching the solidified filaments to achieve molecular orientation, and annealing the drawn filaments to relieve internal stresses.

Barbs may then be formed on a filament utilizing such processes as cutting, injection molding, extrusion, and stamping. For example, barbs may be formed by making angular cuts directly into the suture body, with cut portions pushed outwardly and separated from the body of the suture. Other suitable methods of cutting barbs include the use of a laser or manual methods. With regard to molding barbs, a polymeric filament may be placed within a mold and a molten polymer may be injected into the mold and allowed to cool and solidify to form a barbed suture.

The utilization of a blown film as a barbed suture, and the process of making the same, offers many advantages over the conventional methods of forming barbed sutures. For example, barbs may be cut into the blown film before suture formation for ease of manufacture. Moreover, sutures of different lengths, diameters, and barb configurations may be easily made by varying the length, width, and/or thickness of the blown film, as well as the cuts made therein. Bioactive agents may also be more easily incorporated into the suture, such as by bulk loading, given the larger surface area of the blown film. Additionally, the process may be engineered to be continuous thereby making the cost of production considerably lower than current suture forming methods which are very machine and time intensive.

SUMMARY

The present disclosure relates to methods and systems of forming barbed sutures from blown films. A method for forming a barbed suture in accordance with the present disclosure includes providing a blown film, cutting slits into an outer edge of the blown film, and twisting the blown film such that the slits protrude from the twisted blown film to form a barbed suture. The method may further include stiffening an outer edge of the blown film prior to cutting the slits. The outer edge may be stiffened by heating.

The slits may be formed at acute angles that project toward one end of the blown film to form directional barbs. In embodiments, a first set of slits may project toward one end of the blown film and a second set may project toward another end of the blown film to form bi-directional barbs. In embodiments, the slits may be substantially linear and in other embodiments, the slits may be curved.

The method of forming barbed sutures may further include cutting slits into a second outer edge of the blown film. In embodiments, the slits cut into the first outer edge project toward a first end of the blown film and the slits cut into the second out edge project toward a second end of the blown film to form bi-directional barbs.

The twisted blown film may be stretched to increase the strength of the barbed suture. In embodiments, the twisted film may be heated to ensure that the suture does not unravel. In other embodiments, an adhesive may be utilized to set the barbed suture.

A system for forming a barbed suture in accordance with the present disclosure includes a set of heating rollers configured for stiffening an outer edge of a blown film, a set of cutting rollers configured for forming slits in the outer edge, a set of twisting rollers configured for twisting the blown film into a suture, and a heat source to set the suture. In embodiments, the heat source may be integrated into the set of twisting rollers. In some embodiments, the heat source is an oven.

The system may further include a set of fixed and adjustable rollers configured for stretching the blown film. A set of pinch rollers configured for adjusting the shape of the suture may also be utilized with the system of the present disclosure.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein:

FIG. 3A is a front view of the blown film of FIG. 2 including slits cut into the stiffened outer edge in accordance with the present disclosure;

FIG. 3B is a perspective side view of the blown film of FIG. 3A in a rolled-up configuration in accordance with the present disclosure;

FIG. 4A is a front view of a blown film including bi-directional slits cut into the stiffened outer edge in accordance with another embodiment of the present disclosure;

FIG. 4B is a perspective side view of the blown film of FIG. 4A in a rolled-up configuration in accordance with the present disclosure;

FIG. 5 is a front view of a blown film including compound slits cut into the stiffened outer edge in accordance with yet another embodiment of the present disclosure;

FIG. 6 is a front view of a blown film including curved slits cut into the stiffened outer edge in accordance with another embodiment of the present disclosure;

FIG. 7A is a front view of a blown film including slits pierced into the stiffened outer edge in accordance with another embodiment of the present disclosure;

FIG. 7B is a perspective side view of the blown film of FIG. 7A in a rolled-up configuration in accordance with the present disclosure;

FIG. 8 is a front view of a blown film including two stiffened outer edges in accordance with an embodiment of the present disclosure;

DETAILED DESCRIPTION

Figure 1:
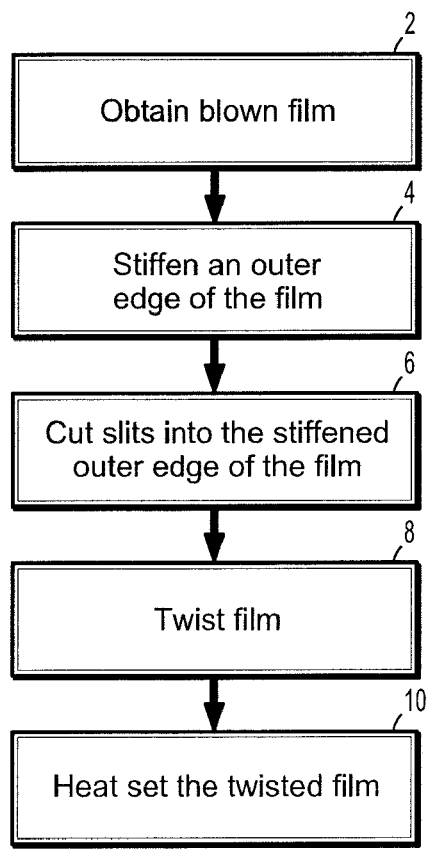
FIG. 1 is a flow chart of a process of forming a barbed suture from a blown film according to one embodiment of the present disclosure.

Barbed sutures in accordance with the present disclosure are formed from blown films. A barbed suture may be created by making slits down an edge of a blown film and twisting the film until the film is rounded and forms a suture body. Once the film starts to take on the rounded shape, the slits on the edge of the film may begin to protrude from the formed body of the suture thereby acting as anchors or barbs.

Embodiments of forming a barbed suture from a blown film will now be described in detail with reference to the drawings wherein like reference numerals identify similar or like elements throughout the several views. Although shown having a circular cross-sectional geometry, the cross-sectional geometry of the suture may be of any suitable shape. For example, the formed suture may be elliptical, square, flat, octagonal, or rectangular.

FIG. 1 is a block diagram illustrating a process for forming a barbed suture from a blown film in accordance with the principles of the present disclosure. Step 2 recites obtaining a blown film. Blown films, as well as machines for making blown films, are well known to the skilled artisan and are commercially available. Alternatively, blown films may be formed via any blown film process as within the purview of those skilled in the art.

An example of a process for forming a blown film is described by Ostapoff et al. in U.S. Patent Publication No. 2010/0059570, the entire contents of which is herein incorporated by reference. Briefly, this technique involves introducing a polymer into an extruder including external heating elements to aid in melting the polymer. The polymer is then transferred to a die from which the polymer is extruded through a circular slit to form a tubular film. The tubular film may be expanded by a compressed gas, such as compressed air, which increases the diameter of the tubular film. Cooling means may then be provided to impart quick and effective cooling and stabilization to the tubular film. After the film is completely cooled and hardened, it is flattened into a sheet of double-thickness film which may be separated into two sheets of film. The sheets of film may then be cut or similarly treated to form a blown film possessing the desired dimensions.

The width and the thickness of the film will vary depending on the size of the suture desired. In embodiments, the blown films may have a width of about 1 centimeter to about 12 centimeters, and a thickness from about 0.0008 millimeters to about 1.5 millimeters.

Alternatively, it is envisioned that the films may be formed utilizing other methods within the purview of those skilled in the art, including for example, the use of compression rollers, contoured rollers, heat pressing, combinations thereof, and the like. Examples of such processes are also described by Ostapoff et al. in U.S. Patent Publication No. 2010/0059570, incorporated by reference above.

Blown films may be formed of degradable materials, non-degradable materials, and combinations thereof. The choice of polymeric material may affect properties of the film, such as thickness, tensile strength, and ductility. Suitable degradable materials which may be utilized to form the blown film include, but are not limited to, natural collagenous materials or synthetic resins including those derived from alkylene carbonates such as trimethylene carbonate, tetramethylene carbonate, and the like, caprolactone, valerolactone, dioxanone, polyanhydrides, polyamides, polyesters, polyacrylates, polymethylmethacrylates, polyurethanes, glycolic acid, lactic acid, glycolide, lactide, polyhydroxy butyrates, polyorthoesters, polyhydroxy alkanoates, homopolymers thereof, copolymers thereof, and blends and combinations thereof.

Suitable non-degradable materials which may be utilized to form the blown films of the present disclosure include, but are not limited to, polyolefins such as polyethylene and polypropylene, including atactic, isotactic, syndiotactic, and blends thereof; copolymers of polyethylene, polypropylene, and ultra high molecular weight polyethylene; polyamides (also known as nylon); polyesters such as polyethylene terephthalate and polybutylene terephthalate; polytetrafluoroethylene; polyether-esters such as polybutester; polytetramethylene ether glycol; 1,4-butanediol; polyurethanes; and combinations thereof.

Figure 2:
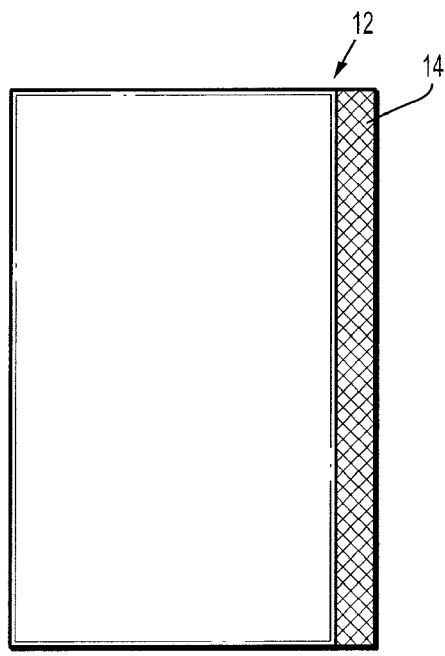
FIG. 2 is a front view of a blown film including a stiffened outer edge in accordance with an embodiment of the present disclosure.

After obtaining a blown film in accordance with the present disclosure, an outer edge 14 of the blown film 12 is then stiffened as stated in step 4 of FIG. 1 and illustrated in FIG. 2. In embodiments, the outer edge may be heated and/or cooled to change the crystallinity of the polymer of the outer edge of the film. A higher crystallinity will increase the stiffness of the outer edge of the film. In some embodiments, the outer edge may be heated and/or cooled to further crosslink the polymer forming the blown film. In yet other embodiments, a crosslinking agent may be applied prior to heating the film to effect crosslinking of the film to thereby stiffen the outer edge. The stiffened edge serves as the matrix for the suture barbs.

Slits 16 are then cut into the stiffened outer edge 14 of the blown film 12 as stated in step 6 of FIG. 1 and illustrated in FIG. 3A. Slits may be cut into the stiffened outer edge of the film via a variety of cutting blades or slitter knives, such as razor slitting blades, rotary shear slitting blades, among others within the purview of those skilled in the art. The slits may be cut into the outer edge of the film at any angle and spacing from each other depending on the number and angle of barbs desired. As illustrated in the embodiment shown in FIG. 3A, the slits 16 are formed at acute angles relative to the body of the blown film 12. All slits 16 project towards one end of the blown film 12 thereby providing directional anchors or barbs 19 after the blown film 12 is rolled or twisted into suture 18 as illustrated in FIG. 3B.

In embodiments, as illustrated in FIG. 4A, multiple slits 26 may be formed in the blown film 22 such that some of the slits 26a are formed at acute angles which project toward one end of the film 22 and the remaining slits 26b are cut at acute angles which project toward the other end of the film 22 so as to form a suture 28 with bi-directional barbs 29 upon suture formation as illustrated in FIG. 4B. Alternatively, a plurality of slits may be formed in the same or random configuration at different angles in relation to each other to form the barbs of the suture.

Optionally, the film may include a plurality of substantially linear or non-linear slits that are spaced at the same or different lengths according to the type of tissue being manipulated and/or procedure that is going to be performed with the formed suture. In some embodiments, the slits 36 of blown film 32 may include two or more angled portions 36' and 36" as illustrated in FIG. 5 or the blown film 42 may include curved slits 46 having one or more points of inflection as illustrated in FIG. 6. Additionally, the film may be cut such that there is a combination of single and compound, linear or curved, slits.

Alternatively, the slits 56 in the blown film 52 may be punched or stamped into the stiffened outer edge 54 as illustrated in FIG. 7A to form a suture 58 including barbs 59 as illustrated in FIG. 7B. It is envisioned that more than one outer edge of the blown film may be stiffened and perforated via any of the techniques and/or configurations as described above. For example, FIG. 8 illustrates a blown film 62 which includes a first stiffened outer edge 64a and a second stiffened outer edge 64b each including slits 66 formed therein to provide bi-directional barbs.

Referring again to FIG. 1, the film is twisted in step 8 to form a suture. The number of times the film is twisted and the orientation of the film upon twisting are dependent upon the properties of the film, such as the thickness and/or width of the film, the placement of the slits in the film, and the desired diameter of the finished suture, for example. Optionally, a stretching operation may be performed prior to, during, or after twisting the film to draw the film thereby increasing the strength of the suture by increasing the molecular orientation of the polymer of the film. The twisted film is then heat set in step 10 so that the blown film forming the suture will not unravel. Alternatively, an adhesive may be applied to the blown film prior to or after slit formation or twisting and allowed to cure and set to form the suture. In some embodiments, the suture may be set by solvent welding.

The blown film may optionally include a bioactive agent. In embodiments, at least one bioactive agent may be combined with the polymer utilized to form the blown film by freely admixing the bioactive agent with the polymer. In other embodiments, the bioactive agent may be tethered to the polymer forming the blown film through any variety of chemical bonds. Alternatively, the bioactive agent may be tethered to the blown film after suture formation. Due to the relatively large surface area of the blown film, greater quantities of select bioactive agent(s) may be delivered with barbed sutures formed from the presently disclosed blown film. Thus, in these embodiments, the blown film can also serve as a vehicle for delivery of a bioactive agent.

The term "bioactive agent," as used herein, is used in its broadest sense and includes any substance or mixture of substances that have clinical use. Consequently, bioactive agents may or may not have pharmacological activity per se, e.g., a dye. Alternatively a bioactive agent could be any agent which provides a therapeutic or prophylactic effect, a compound that affects or participates in tissue growth, cell growth, cell differentiation, an anti-adhesive compound, a compound that may be able to invoke a biological action such as an immune response, or could play any other role in one or more biological processes.

Examples of classes of bioactive agents which may be utilized in accordance with the present disclosure include anti-adhesives, antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, platelet activating drugs, clotting factors, and enzymes. It is also intended that combinations of bioactive agents may be used.

Other bioactive agents include: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; antiparkinson agents such as L-dopa; anti-spasmodics; anticholinergic agents (e.g., oxybutynin); antitussives; bronchodilators; cardiovascular agents such as coronary vasodilators and nitroglycerin; alkaloids; analgesics; narcotics such as codeine, dihydrocodeinone, meperidine, morphine and the like; non-narcotics, such as salicylates, aspirin, acetaminophen, d-propoxyphene and the like; opioid receptor antagonists such as naltrexone and naloxone; anti-cancer agents; anti-convulsants; anti-emetics; antihistamines; anti-inflammatory agents such as hormonal agents, hydrocortisone, prednisolone, prednisone, non-hormonal agents, allopurinol, indomethacin, phenylbutazone and the like; prostaglandins and cytotoxic drugs; chemotherapeutics; estrogens; antibacterials; antibiotics; anti-fungals; anti-virals; anticoagulants; anticonvulsants; antidepressants; antihistamines; and immunological agents.

Other examples of suitable bioactive agents, which may be included in the blown film of the present disclosure include, for example, viruses and cells; peptides, polypeptides and proteins, as well as analogs, muteins, and active fragments thereof; immunoglobulins; antibodies; cytokines (e.g., lymphokines, monokines, chemokines); blood clotting factors; hemopoietic factors; interleukins (IL-2, IL-3, IL-4, IL-6); interferons (β-IFN, α-IFN and γ-IFN); erythropoietin; nucleases; tumor necrosis factor; colony stimulating factors (e.g., GCSF, GM-CSF, MCSF); insulin; anti-tumor agents and tumor suppressors; blood proteins such as fibrin, thrombin, fibrinogen, synthetic thrombin, synthetic fibrin, synthetic fibrinogen; gonadotropins (e.g., FSH, LH, CG, etc.); hormones and hormone analogs (e.g., growth hormone); vaccines (e.g., tumoral, bacterial and viral antigens); somatostatin; antigens; blood coagulation factors; growth factors (e.g., nerve growth factor, insulin-like growth factor); bone morphogenic proteins; TGF-B; protein inhibitors; protein antagonists; protein agonists; nucleic acids such as antisense molecules, DNA, RNA, RNAi; oligonucleotides; polynucleotides; and ribozymes.

Figure 9A:
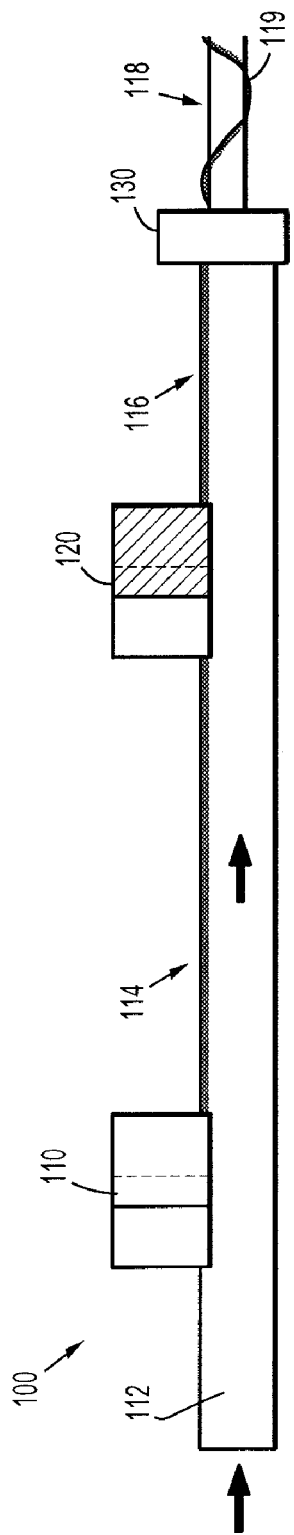
FIG. 9A is a schematic top plan view of an apparatus which is suitable for carrying out the manufacture of a barbed suture from a blown film in accordance with the present disclosure.
Figure 9B:
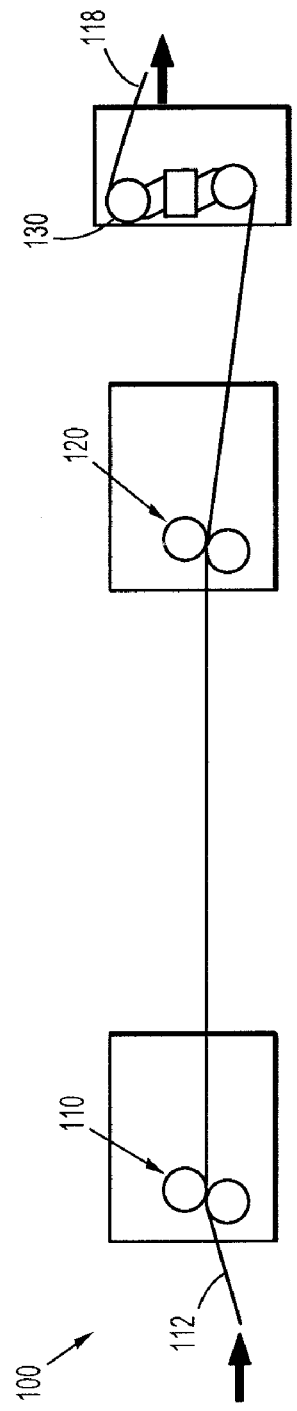
FIG. 9B is a schematic side plan view of the apparatus of FIG. 9A.

An embodiment of a system for transforming the blown film into a barbed suture will now be described with reference to FIGS. 9A and 9B. System 100 includes heating rollers 110, cutting rollers 120, and twisting rollers 130. An outer edge 114 of blown film 112 is passed over a set of heating rollers 110 to heat the outer edge 114 and make the outer edge 114 slightly stiffer than the rest of the blown film 112. In embodiments, the crystallinity of the outer edge 114 is increased by about 5% to about 35% over the crystallinity of the remainder of the film. In embodiments, the crystallinity of the outer edge is about 10% to about 30% greater than the crystallinity of the remainder of the film and in some embodiment, the crystallinity is about 20% greater.

The outer edge 114 of blown film 112 is then passed over a set of cutting rollers 120. The cutting rollers 120 place slits 116 into the outer edge 114 of blown film 112 that was stiffened by heating rollers 110. As illustrated, slits 116 may be cut into the blown film 112 on a diagonal to form directional barbs.

The blown film 112 is then rolled on twisting rollers 130. The blown film 112 is passed over rollers that are set about 90 degrees apart from each other. As the blown film 112 is passed over each roller a twist is introduced to the material. The blown film 112 is twisted such that the slits 116 protrude from the formed suture body 118 and the cut outer edge form barbs 119 on the suture 118.

Optionally, the blown film 112 may be stretched prior to, during, or after the twisting operation to increase the strength of the formed suture. The blown film may be stretched by passing the film through a set of fixed and adjustable rollers whereby movement of the adjustable rollers, relative to the fixed rollers, causes the film to lengthen. Stretching of the film may also be achieved by drawing the blown film through hot water (or other suitable liquid medium) by means of rollers which rotate at different speeds to provide the desired stretch ratio to the film.

The twisted blown film 112 is then heat set to maintain the shape of the suture. The film may be heated to about the glass transition temperature of the polymeric material forming the blown film. In embodiments, twisting rollers 130 may be heated for substantially simultaneous heating of the blown film 112 as it is passed through twisting rollers 130. In some embodiments, an external heating source may be placed around the twisting rollers 130, or in close proximity thereto, to heat set the twisted blown film. In other embodiments, the twisted blown film 112 may be passed through an oven and optionally run through a set of pinch rollers while the material is still warm and maleable to set the suture. The processed material may then be wound onto spools via take-up winders for subsequent processing, such as sterilization and/or packaging.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure. Additionally, it is envisioned that the elements and features illustrated or described in connection with one exemplary embodiment may be combined with the elements and features of another exemplary embodiment, without departing from the scope of the present disclosure, and that such modifications and variations are also intended to be included within the scope of the present disclosure. Accordingly, the subject matter of the present disclosure is not to be limited by what has been particularly shown and described, as modifications and variations are intended to come within the scope and spirit of the claims appended hereto.

What is claimed is:

1. A method of forming a barbed suture, the method comprising the steps of:
    providing a blown film;
    stiffening an outer edge of the blown film to increase the crystallinity of the outer edge over a remainder of the film;
    cutting slits into the outer edge of the blown film; and
    twisting the blown film to form a barbed suture.

2. The method according to claim 1, wherein cutting slits includes forming the slits at acute angles which project toward a first end of the blown film.

3. The method according to claim 2, wherein the slits are substantially linear.

4. The method according to claim 2, wherein the slits are curved.

5. The method according to claim 1, wherein cutting slits includes forming a first set of slits at an acute angle which project toward a first end of the blown film and forming a second set of slits at an acute angle which project toward a second end of the blown film.

6. The method according to claim 1, further comprising the step of cutting slits into a second outer edge of the blown film.

7. The method according to claim 6, wherein the slits cut into the first outer edge project toward a first end of the blown film and the slits cut into the second outer edge project toward a second end of the blown film.

8. The method according to claim 1, wherein cutting slits includes cutting a first portion of the slit at a first angle and cutting a second portion of the slit at a second angle.

9. The method according to claim 1, wherein stiffening the outer edge of the blown film includes heating the outer edge.

10. The method according to claim 1, further including the step of stretching the blown film.

11. The method according to claim 1, further including the step of heating the twisted blown film to set the barbed suture.

12. The method according claim 1, further including the step of applying an adhesive to set the barbed suture.

13. The method according to claim 1, wherein providing the blown film further includes forming the blown film from a degradable material.

* * * * *